(12) United States Patent
Govaerts et al.

(10) Patent No.: US 9,984,210 B2
(45) Date of Patent: May 29, 2018

(54) METHOD FOR MAKING RADIOGRAPHS WITH DIRECT RADIOGRAPHIC PANELS

(71) Applicant: AGFA HEALTHCARE, Mortsel (BE)

(72) Inventors: Wim Govaerts, Mortsel (BE); Patrick Pandelaers, Mortsel (BE)

(73) Assignee: AGFA HEALTHCARE NV, Mortsel (BE)

( * ) Notice: Subject to any disclaimer, the term of this patent is extended or adjusted under 35 U.S.C. 154(b) by 140 days.

(21) Appl. No.: 14/889,266

(22) PCT Filed: May 27, 2014

(86) PCT No.: PCT/EP2014/060934
§ 371 (c)(1),
(2) Date: Nov. 5, 2015

(87) PCT Pub. No.: WO2014/191402
PCT Pub. Date: Dec. 4, 2014

(65) Prior Publication Data
US 2016/0085934 A1    Mar. 24, 2016

(30) Foreign Application Priority Data
May 30, 2013   (BE) ................................. 2013/0381

(51) Int. Cl.
*H05G 1/64* (2006.01)
*G06F 19/00* (2018.01)
*A61B 6/00* (2006.01)

(52) U.S. Cl.
CPC .......... *G06F 19/3412* (2013.01); *A61B 6/461* (2013.01); *A61B 6/563* (2013.01)

(58) Field of Classification Search
CPC ........... A61B 6/00; A61B 6/461; A61B 6/563; A61B 6/46; A61B 6/566; A61B 6/4405; G06F 19/00; G06F 19/3412; G06F 19/32; G06F 19/321; G06F 19/322; G06F 19/323; G06F 19/324; G06F 19/327; G06F 19/34

USPC ..... 378/91, 98, 98.2, 98.5, 98.8, 210; 705/2, 705/3
See application file for complete search history.

(56) References Cited

U.S. PATENT DOCUMENTS

| | | | |
|---|---|---|---|
| 7,979,287 B2 | 7/2011 | Amitani et al. | |
| 8,031,837 B2 | 10/2011 | Spahn | |
| 8,325,875 B2 | 12/2012 | Omernick et al. | |
| 8,396,188 B2 * | 3/2013 | Liu | A61B 6/4233 378/62 |
| 2013/0121468 A1 | 5/2013 | Ohta et al. | |
| 2015/0181629 A1 * | 6/2015 | Jun | H04W 76/021 455/420 |

FOREIGN PATENT DOCUMENTS

| | | |
|---|---|---|
| WO | 2012/014661 A1 | 2/2012 |
| WO | 2012/046092 A1 | 4/2012 |

OTHER PUBLICATIONS

Official Communication issued in corresponding International Application PCT/EP2014/060934, dated Jul. 2, 2014.

* cited by examiner

*Primary Examiner* — Jurie Yun
(74) *Attorney, Agent, or Firm* — Keating and Bennett, LLP

(57) ABSTRACT

A method for performing a job list of radiographic recordings indicated in a radiographic information systems includes communicating the job list to a mobile apparatus, e.g. a smartphone, whereby, in a first step, a peer-to-peer communication is set up between the radiographic information system and the mobile apparatus by a Near Field Communication technique, whereupon the job list is transmitted to the mobile apparatus via a WIFI peer-to-peer communication. A radiographer then completes the job list by using, inter alia, a self-triggering direct radiographic panel and a radiographic generator.

8 Claims, No Drawings

METHOD FOR MAKING RADIOGRAPHS WITH DIRECT RADIOGRAPHIC PANELS

CROSS-REFERENCE TO RELATED APPLICATIONS

This application is a 371 National Stage Application of PCT/EP2014/060934, filed May 27, 2014. This application claims the benefit of Belgian Application No. 2013/0381, filed May 30, 2013, which is incorporated by reference herein in its entirety.

BACKGROUND OF THE INVENTION

1. Field of the Invention

The present invention relates to an improved method for making radiographs by direct radiographic panels.

More in particular, the method relates to a technique in which the communication between the direct radiographic panel, a mobile radiographic generator, a radiographic workstation, and a mobile apparatus operated by the radiographer is improved.

The major advantage of a method according to the invention is an enhanced operational convenience for the radiographer doing his round of patients for whom a radiograph is to be made.

2. Description of the Related Art

It is known that X-rays have important applications in the field of medical imaging in which the medical-diagnostic benefit for the patient mostly largely outweighs the small and limited risk of radiation damage.

Originally, mostly silver halide-based radiographic film was used as a registration medium for radiographic recording.

However, during the last decades, so-called computed radiography (CR) has increasingly gained interest. This technique uses a radiographic plate in which silver halide has been replaced as light-sensitive element by so-called storage phosphors.

This method is extensively described in, for example, the Handbook of Medical Imaging (ed. R. V. Matter et al., SPIE Press, Bellingham, 2000).

However, since a couple of years, direct digital radiographic techniques, known as DR (Direct Radiography), are increasingly used for radiographic recording.

This method is increasingly used as an alternative to film-based imaging techniques as well as to the above-mentioned panels based on stimulable phosphor or storage phosphor technologies.

In this direct digital radiography technique, the radiographic exposure energy is fixed pixel-wise in a radiographic sensitive panel and thereupon converted into electronic image data by electronic components. Subsequently, the information is read out image-wise and displayed on an appropriate monitor in order to allow a radiologist to make a diagnosis.

One of the driving forces behind the success of direct digital radiography is the ability to rapidly visualize the obtained radiographic images and to communicate them in a simple and efficient manner by data networks to one or more locations in order to be remotely analyzed and diagnosed by a radiologist or other medical expert. Thanks to this technique, the delays that typically occur in developing, packing and physically sending radiographic films, as well as the inconvenience related to scanning developed films and the corresponding loss of resolution, are avoided.

Direct radiographic (DR) systems have the advantage, compared to computer radiography (CR) systems based on storage or stimulable phosphors, that the latent stored radiographic image does not have to be read out (in a digitizer). On the contrary, the digital radiographic image can immediately or directly be read out in order to make the radiographic diagnosis. This diagnosis can then be carried out on a local workstation as well as on a very remotely located workstation.

Originally, the first direct radiographic panels were integrated into the complete radiographic imaging system. The wiring and cabling was then provided in a manner which minimizes the disturbance for the radiographer when putting in place the direct radiographic panel for recording a body part of the patient.

More recently, portable direct radiographic panels have been introduced into the market. These panels use built-in batteries and wireless communication with the radiographic control panel or workstation, as well as with the data storage device and display components.

Thanks to the last-mentioned aspects, such portable wireless panels can be used in a very flexible way and are very appropriate for use in a fully digital radiographic recording system.

They can be used in a hospital or a medical diagnostics centre as well as in a completely new installed radiographic imaging system, or in a so-called retrofit situation. The term "retrofit" is to be understood here as an existing radiographic imaging system which previously used radiographic films or stimulable or storage phosphor imaging plates and in which the latter recording devices are replaced by a direct radiographic storage medium, a so-called direct radiographic or DR panel, without, for example, the workstation or the radiography source itself having to be replaced.

The advantage of a retrofit radiography system, compared to a completely new installed direct radiography system, lies in its lower investment cost since part of the existing radiographic station can be kept.

Although portability and wireless communication of the radiographic storage medium are an obvious advantage when using portable and wireless DR panels, these features, however, also cause potential problems in practical conditions of use.

One of the problems encountered when using such panels, is the fact that, once the recording is finished, the stored radiographic image cannot, or only difficultly, be sent to the radiographic console due to transmission difficulties with the available wireless network.

A further drawback relates to the fact that when the radiographer does his round of the different patients for whom a radiograph is to be made at the healthcare institution, the radiographer does not have a complete job list of the radiographs to be made.

Thus, also in a situation in which, for example, the radiographic image is stored on the direct radiographic panel, the radiographer cannot proceed to the next recording until he has consulted said job list on the radiographic workstation that's is connected to the Hospital Information System (HIS) which comprises the Radiological Information System (RIS).

In U.S. Pat. No. 8,031,837 B2, published on Oct. 4, 2011, assigned to Siemens A G, Munich, Germany, a mobile or portable control and monitoring unit is described for use in a radiology department. This represents an improvement over the formerly known stationary control units that were fixedly built-in or constituted an inseparable part of the radiographic system itself.

According to column 2, lines 66-67, of this patent, such an apparatus can also be used to control the radiographic process and processing process.

According to column 3, lines 64-67, of this patent, both said portable monitor unit and the digital DR panel can be equipped with a wireless connection for exchange of data.

According to column 3, lines 42-44, the mobile control unit can be equipped with image processing software for post-editing the radiographic images which have been received from the digital DR panel.

The above-described wireless communication unit allows to also connect such a mobile control unit to databases, such as a Picture Archiving and Communications System (PACS), as well as to an in-hospital Radiological Information System (RIS) (column 3, lines 58-63, and claim 1, column 4, lines 40-41).

However, the device as described herein is intended to smoothly perform a specific remote controlled radiograph for a patient from such a unit. The functionality as incorporated in a fixed control unit in the prior art, as described in FIG. 1 of this patent, is incorporated herein, without further reference, in a corresponding portable control device.

The above-described drawbacks are thus not solved in any way by the mobile control apparatus proposed in this patent and there is neither any proposal nor any hint to adapt or use the device for such purposes.

In U.S. Pat. No. 8,325,875 B2, published on Dec. 4, 2012, assigned to General Electric Company, a mobile device for radiography is described. This mobile radiography device is equipped with a so-called 'portable image processing system' that controls the radiographic recording.

However, the term 'portable' is to be understood here as an apparatus which is mounted on a mobile radiography device or a radiography device which can be moved by a carriage. This apparatus also has the ability to wirelessly communicate with the DR Panel. A wireless communication possibility with a PACS/RIS/HIS is described in column 3, lines 37-43, of the specification and is also illustrated on the bottom of FIG. 2.

However, the above-mentioned problems aren't solved either by the embodiments described in said patent application.

Moreover, there is neither any proposal nor any hint to adapt or use the device as described in said patent for such purposes.

In U.S. Pat. No. 7,979,287 B2, published on Jul. 12, 2011, assigned to Konica Minolta Medical & Graphic, a radiographic image system is described, wherein a doctor uses a PDA (Personal Digital Assistant) during his 'radiograph round'. This PDA has the so-called 'radiographing order information' stored in it, which prevents confusion between radiographic patients and radiographic image data.

This system is applied in so-called 'large-scale' systems that use computer radiography (CR), but also Digital DR panels (column 1, lines 44-52).

In this configuration, the above-mentioned radiographing order information is transmitted from a radiographic control apparatus to the PDA. According to FIG. 1(*b*), the PDA is connected to the radiographic control apparatus via a 'cradle', indicated as element 10 *a/b*. In column 29, lines 28-35, the function of this PDA is explained. The PDA receives the radiographing order information from the connected control apparatus via said cradle and to visualize it to the radiographer.

The above-described drawbacks are thus not solved in any way by the mobile control apparatus proposed in said patent and there is neither any proposal nor any hint to adapt or use the device for such purposes.

SUMMARY OF THE INVENTION

Preferred embodiments of the present invention respectively prevent and solve the above-described drawbacks and problems.

The above-mentioned advantages and aspects are realized by a method as described below.

Specific features of preferred embodiments of the invention are also set out below.

Further advantages and embodiments of the present invention will become apparent from the following description.

DETAILED DESCRIPTION OF THE PREFERRED EMBODIMENTS

The present invention relates to a method or process for performing a radiograph job list indicated in a radiographic information system, comprising the following steps:

communicating said job list from the radiographic information system to a mobile apparatus;

performing radiographs from the job list and storing the images on a direct radiographic panel;

inspecting a performed radiograph on a display of the mobile apparatus before proceeding to a next radiographic recording indicated in the job list;

communicating the radiographs stored on the direct radiographic panel to an image management and communication system.

According to a preferred embodiment of the method according to the invention, the said job list is communicated from the radiographic information system to the mobile apparatus by setting up, in a first step, a peer-to-peer communication between the radiographic information system and the mobile apparatus by using a Near Field Communication technique, whereupon in a next step, the said job list is transmitted from the radiographic information system to the mobile apparatus via a WIFI peer-to-peer communication.

Further preferred embodiments of the invention are set out below.

The proposed invention and the preferred embodiments of the invention, respectively, relate(s) to a method (workflow) which can comprise the following elements:

A job list for the radiographer, generated in a Radiological Information System;

A direct radiographic panel which is preferably self-triggering and/or wireless, hereinafter referred to in short as DR panel;

A mobile device or apparatus of the type tablet PC or smartphone, hereinafter referred to in short as smartphone;

A radiographic workstation, for example, the workstation marketed by Agfa Healthcare under the trade name Agfa NX, hereinafter referred to in short as workstation.

A mobile generator for generating radiographic radiation.

These different elements will be described hereinafter in a more detailed manner.

Mobile Apparatus

In the concept according to a preferred embodiment of the invention, the radiographic recordings are controlled by a mobile apparatus operated by the radiographer. This mobile apparatus has to comprise at least the following functionalities:
- the ability to process and store radiographic images and data and to visualize them on a screen;
- the ability to receive and transmit orders resp. from or to the user, in this case the radiographer, preferably via a touch screen;
- the ability to wirelessly communicate, inter alia with the DR Panel.
- the ability for the operator to easily hold it in his hand when handling it.

Optionally, the mobile apparatus is also equipped with a telephone communication connection, however, this is not essential to the application of the present invention.

Such a mobile apparatus can, for example, be chosen from one of the devices in the following list: a hand-operated computer in one of the following forms: a laptop, a notebook, an ultrabook, a netbook, a computer with touch screen (type i-Pad), a smartphone, a personal digital assistant (PDA), certain types of e-readers, and more generally any multi-function mobile apparatus which supports wireless communication, as well as any kind of multi-function telephone, provided that the above-mentioned functionalities are available on this mobile apparatus.

Preferably, a computer is used with a touch screen because of its operational ease.

The term 'smartphone' is to be understood here as a hand-operated computer or personal digital assistant which at the same time is also a telephone, thus a mobile apparatus offering several of the advanced applications which are also available on a personal computer, such as electronic mail communication, high speed internet access, audio and video representation options, advanced interaction techniques, for example via touch screens, GPS functionality and possibly more of such services.

For the sake of simplicity of description, a smartphone will always be referred to as an example of such wireless communication device of the user in the following description. It is, however, obvious that any of the above-mentioned mobile apparatuses can be used instead of a smartphone without departing from the scope of the present invention.

The hand-operated computer or smartphone communicates inter alia with the wireless DR panel via the built-in communication module and via a wireless communication network for data transmission.

Connection with RIS

In order to make the job list available to the radiographer, a kind of integration or operational connection between, on the one hand, the RIS System which is available in the healthcare institution (e.g. the hospital) and, on the other hand, the workstation of the smartphone is necessary.

The term 'RIS system" is to be understood as a Radiological Information System such as the RIS system as marketed, for example, by Agfa Healthcare to healthcare institutions under the trade name Impax RIS.

Loading RIS info into the Smartphone

For the application of a preferred embodiment of the present invention, preferably use is made of 'Near Field Communication' technology (hereinafter referred to as NFC) in order to load the RIS information that is relevant for the radiographer from the workstation into the smartphone.

However, the respective RIS info itself does not have to be communicated per se via NFC. According to a preferred embodiment of the present invention, NFC can, for example, be a way to set up a Peer-2-Peer (hereinafter referred to as P2P) communication via WiFi between the smartphone and the radiographic workstation, in order to subsequently transmit the respective relevant RIS information via this P2P communication.

The main reason why the transfer of the relevant RIS information itself occurs via P2P rather than via NFC, is because wireless communication via P2P is usually quicker than via NFC.

The respective RIS-info can, for example, comprise the job list, i.e. the list of the radiographs that are to be performed during a certain period, during a day or a part of a day, by the radiographer.

This RIS job list contains, for example, the list of the patients for whom such radiographs are to be made, including their demographic data, as well as the type of recording(s) to be performed for each of these patients.

NFC Technology

The term 'Near Field Communication' is to be understood as a short-distance wireless communication technology that enables the exchange of data between devices over a distance up to 4 inches or approximately 10 cm.

The NFC technology has been developed and standardized by the NFC forum, with inter alia Nokia, Philips and Sony as members. It is primarily intended for use in mobile phones, for example smartphones.

Examples of mobile phones equipped with NFC are Google Nexus S, Nokia N9, Nokia Lumina 920, Nokia 6131, Nokia 6212 Classic, Samsung Star S 5230N, Samsung Galaxy S3, as well as different Sony and HTC devices.

NFC combines the interface of a smart card and a reader in one single device. An NFC device can communicate on the basis of several RFID standards, such as used in the existing ISO/IEC 14443 smart cards and readers, as well as with other NFC devices. It is compatible with existing wireless infrastructure and is primarily intended for use in mobile phone devices.

An NFC chip can operate in three different modes: tag-emulation, or passive mode, active mode in which the NFC chip behaves as a reader, or a peer-to-peer mode in which it is possible to communicate between two NFC devices for the purpose of, for example, data transmission.

Transmission of RIS Data From the Workstation to the Smartphone Via NFC or via WiFi Peer-2-Peer As indicated above, for the application of a preferred embodiment of the present invention, the latter method is the adequate method in which the NFC technology is used for the application of the present invention. In this method, the smartphone that is equipped with the NFC technology is kept at a distance of about 3 to 5 cm from the workstation that is also equipped with an NFC chip or an external NFC device that is plugged into the workstation.

Said method allows data to be exchanged in a simple and wireless manner between the workstation and the smartphone and, for example, the RIS job list to be read from the radiographic workstation into the memory of the smartphone.

As soon as the RIS information is loaded into the smartphone in the manner described above, the radiographer can start his round of the patients.

Radiographer on His Round

The moment a radiographer visits a patient, he will retrieve the respective patient from the RIS job list on his smartphone as well as check the type of radiograph that is prescribed for the specific patient.

Identification of the Patient

The identification of the patient can be carried out in many ways.

According to a first option, the patient identifies himself by giving his name when requested by the radiographer.

According to another possibility, the patient wears a wristband or ankle band that is provided with the required identification data.

These data can be, for example, the name of the patient or similar demographic information or a bar code or QR code that is scanned by the smartphone of the radiographer, or a combination of the said methods. Optionally, the patient's wristband or ankle band can also be provided with an NFC chip.

Another method consists in indicating the demographic data of the patient on the bed on which the patient lies.

A combination of the said techniques can possibly be used for an unambiguous identification of the patient.

Radiographic Recording

As soon as the identity of the patient has been determined and the type of radiograph has been visualized from the RIS list, the actual radiographic recording can be performed.

For the application of a preferred embodiment of the present invention, the radiographic DR panel has to be set in self-triggering mode. This allows the DR panel to detect and capture an image. For the application of a preferred embodiment the present invention, the term "self-triggering radiographic DR panel" is to be understood as a DR panel which does not require a synchronization with the radiographic generator.

If the method according to a preferred embodiment the present invention is applied, for example, by a so-called retrofit radiographic system, such a self-triggering radiographic DR Panel is required.

The term 'retrofit radiographic system' for the application of a preferred embodiment the present invention is to be understood as the retrofit radiographic system as described hereinbefore in the present patent application.

Examples of retrofit radiographic systems are described inter alia in EP patent 2 209 422, assigned to Carestream Health, Inc. NY, USA.

Communication between the Smartphone and the DR Panel

When using a self-triggering DR panel, a wireless connection between the DR panel and the smartphone must first be established.

To that end, a WI-FI peer-to-peer connection is established between both components.

This connection is set up by first exchanging network data via another channel (e.g. via NFC), contrary to the common methods for establishing a wireless communication between a DR panel and a radiographic workstation in which the WI-FI connection typically is realized via an access point (router).

The term 'WI-FI' is to be understood as a group of IEEE 802.11 standards for wireless communication techniques that use the same base protocol. Wi-Fi is used, inter alia, for creating wireless LANs (Local Area Networks) for computer communications Direct Radiographic Panel For the purposes of a preferred embodiment the present invention, use is preferably made of a self-triggering direct radiographic panel, hereinafter referred to as DR panel. More preferably, use is made of a wireless self-triggering DR Panel. When using this type of DR panel, no synchronization with the radiographic generator is required. Such a type of DR Panel is described, for example, in the following patent (applications): U.S. Pat. Nos. 8396188, 7211802 and EP 1746442. Such panels are marketed, for example, by the company Konica Minolta Medical Imaging U.S.A., Inc., under the trade name AeroSYNC, or by FujiFilm Corporation under the trade name FDR D-EVO plus C35i/s.

For the purposes of a preferred embodiment the present invention, use is also made of a DR panel that allows storing a minimum number of radiographs in its memory. The minimum storage capacity of the DR panel must be about five radiographs, preferably 10, more preferably 50, 100 or more.

The DR panel presented by Trixell/Thales at the RSNA exhibition (Radiological Society of North America) in Chicago in 2012 under the name PIXIUM Portable 3543 EZ has, for example, a memory capacity which allows storing up to 50 images having a size 35×42 cm or 130 images having a size 24×30 cm. Moreover, such a panel offers the possibility of reducing the recording time between consecutive radiographic recordings to 6 seconds.

A radiographic image signal as recorded and stored in the memory of a DR Panel is characterized by a pixel image matrix (pixel array size) of, for example, 3 072×3 072×2 bytes, i.e. 18 874 368 bytes, or slightly less than 20 Mbytes.

For the application of a preferred embodiment the present invention, different sizes of DR panels can be used, such as, inter alia, 10×12", 14×17" and 17×17".

The flat panel detector which is marketed by Konica Minolta under the trade name AeroDR is, for example, available in two sizes, i.e. an 14×17 inch panel having an image size of 1 994×2 430 pixels, or an 17×17 inch panel having an image size of 2 428×2 428 pixels.

For the purposes of a preferred embodiment the present invention, use is also made of a DR panel that is equipped with an internal battery (on-board battery), which allows making a minimum number of radiographs without having to recharge the battery, for example, by placing it in a so-called docking station. The above-mentioned DR panel of Konica Minolta is, for example, characterized in that, with a fully charged battery and under normal operational conditions, the number of radiographs which can be processed without having to recharge the battery, is 200 images in the case of an 14×17 inch panel and 173 images in the case of an 17×17 inch panel.

Preview

Before the radiographer can start a next radiographic recording, he has to know, after each radiograph, whether the recording stored on the radiographic DR panel meets the necessary quality requirements. For the purposes of a preferred embodiment the present invention, this control of the radiograph can be performed at least by a preview of the image of the previous radiograph.

In order to have such a preview offering an image which can be assessed in a meaningful way by the radiographer, image processing comprising the following components is required:
- an offset correction;
- a gain correction;
- an image enhancement, optionally in the form of a slimmed-down or simplified version of the image processing software marketed by Agfa Healthcare under the trade name 'MUSICA'.

The first two components represent the actual preprocessing. Common image processing also comprises 'defect pixel correction', clipping and other preprocessing steps.

MUSICA is the abbreviation for 'Multi-Scale Image Contrast Amplification' and is recognized de facto by the market as the standard for image processing applied to radiographic images. This software is marketed by Agfa Healthcare N.V.

Preview on the Smartphone

After performing the radiographic recording, a preview of the radiographic image stored in the DR panel has to take place.

This preview can be done by visualizing a simplified radiographic image in a display that is integrated in the DR panel, or—preferably—on the display of the smartphone, or optionally on a combination of both devices.

If the panel comprises an integrated display, the method and associated workflow as described in a preferred embodiment the present patent application can be performed without using a smartphone.

The RIS data that are relevant for the radiographer, as well as the identification of a patient, are subsequently stored on the DR panel, whereupon the assessment of the radiographic preview images is performed on the DR display itself.

Optionally, the smartphone can also be used as 'thin client' visualization medium since the browser of the smartphone allows to retrieve and visualize a radiographic image that is simplified by the DR panel for displaying purposes.

Next Radiographic Recording, Finishing the Patients' Round

If the radiographer, when assessing the preview image, determines that the radiograph meets the predefined quality requirements, the next radiograph in the RIS list can be performed.

This can be a next recording of the same patient or a radiograph of a next patient.

If the radiographer, when assessing the preview image, determines that the radiograph does not meet the predefined quality requirements, a so-called retake is to be performed, i.e. a repetition of the radiographic recording that has already been performed previously, possibly with modified radiographic parameters.

With each recording, the radiographic image is stored in the (buffer) memory of the DR panel, together with the demographic data of the patient, and possibly together with detailed data of the radiographic recording.

After the radiographer has completely finished his round, i.e. after he has performed all radiographic recordings listed in the RIS file for the respective period or department or operator, the next phase of the method according to a preferred embodiment the invention is implemented.

Connection with PACS

For the purposes of a preferred embodiment the present invention, preferably use is made of a radiographic workstation that is connected to a PACS system of the healthcare institution. More preferably, the radiographic images are loaded into the PACS system via the DICOM protocol (DICOM represents an industry standard communication protocol for the exchange of medical images and information between computers and computer peripherals. For more info, see Horii et al., "DICOM, An Introduction to the standard").

Such a connection has the advantage that the radiographic images recorded on the DR panel are made available, via the radiographic workstation and its connection with the PACS system, to those operators in the healthcare institution who are authorized to consult and diagnostically assess the radiographs.

As stated hereinbefore, this requires a connection to or an integration with the PACS system of the healthcare institution.

PACS means 'Picture Archiving and Communication System' and represents a global electronic system that is implemented in a healthcare institution for archiving radiographic and other diagnostic images and communicating and visualizing these to the respective departments or operators.

Such a system is offered by several operators, for example, by Agfa Healthcare under the trade name IMPAX.

Such a PACS system is described, for example, in U.S. Pat. No. 6,574,629, assigned to Agfa Corporation, Wilmington, USA, on Jun. 2, 2003.

Transmission of Radiographic Images to PACS

In this step, the radiographs stored in the DR panel are transmitted to the workstation or, via the workstation, transmitted to the PACS system of the healthcare institution.

In order to transmit the radiographic images that are stored in the DR Panel together with the associated metadata in the PACS system, the DR panel is connected to the radiographic workstation.

The images are then read out via this workstation and forwarded to the PACS system via this channel.

To that end, the DR Panel can be connected to the workstation via a physical cable or via a docking station, or via a wireless connection, preferably a WiFi connection.

In case of a wireless configuration, the DR panel can be connected to the radiographic workstation via a peer-to-peer connection or via an access point. In case of a wired connection, the DR panel is connected directly to the workstation.

The invention claimed is:

1. A method for performing radiographic jobs included in a radiographic job list in a radiographic information system, the method comprising the steps of:
   communicating the job list from the radiographic information system to a mobile apparatus;
   performing a radiographic exposure corresponding to one of the radiographic jobs included in the job list and storing a radiographic image on a direct radiographic panel;
   inspecting the radiographic image on a display of the mobile apparatus before proceeding to a next one of the radiographic jobs included in the job list; and
   communicating the radiographic image stored on the direct radiographic panel to an image management and communication system; wherein
   the job list is communicated from the radiographic information system to the mobile apparatus by setting up, in a first step, a peer-to-peer communication between the radiographic information system and the mobile apparatus by using a Near Field Communication technique, and, in a second step, the radiographic image is transmitted from the direct radiographic panel to the mobile apparatus via a WIFI peer-to-peer communication.

2. The method according to claim 1, wherein the job list includes at least information including: demographic data of a patient for whom a radiograph is to be made, and adjustment parameters for a radiographic recording listed in the job list.

3. The method according to claim 1, wherein the direct radiographic panel is a self-triggering radiographic panel.

4. The method according to claim 3, wherein the direct radiographic panel is a wireless self-triggering panel.

5. The method according to claim 1, wherein the step of inspecting the radiographic image on a display of the mobile apparatus is performed based on a preview of the radiographic image.

6. The method according to claim 5, wherein the preview of the radiographic image has been subjected to an offset and gain correction.

7. The method according claim 1, wherein the job list is communicated to the mobile apparatus from a radiographic workstation that is operationally connected to the radiographic information system.

8. The method according to claim 1, wherein, before proceeding to the next one of the radiographic jobs included in the job list, an identity of a patient is indicated according to demographic data included in the job list.

* * * * *